U S 0 0 5 9 8 5 5 6 6 A

US005985566A

United States Patent [19]
Houthoff et al.

[11] Patent Number: 5,985,566
[45] Date of Patent: *Nov. 16, 1999

[54] PLATINUM-CONTAINING COMPOUNDS, METHODS FOR THEIR PREPARATION AND APPLICATIONS THEREOF

[75] Inventors: Hendrik J. Houthoff, Amsterdam; Jan Reedijk, Leiden; Tinka Jelsma, Almere; Remco Maria Van Es, Zaan; Franciscus Michiel van den Berg, Hoofddorp; Edwin Leo Mario Lempers, Julianadorp; Marieke Johanna Bloemink, Oegstgeest, all of Netherlands

[73] Assignee: Kreatech Diagnostics, Amsterdam, Netherlands

[*] Notice: This patent is subject to a terminal disclaimer.

[21] Appl. No.: 08/910,070

[22] Filed: Aug. 12, 1997

Related U.S. Application Data

[63] Continuation of application No. 08/470,265, Jun. 6, 1995, Pat. No. 5,714,327, which is a continuation-in-part of application No. 07/975,586, Oct. 19, 1993, Pat. No. 5,580,990.

[30] Foreign Application Priority Data

Jul. 19, 1990 [NL] Netherlands ............ 90 01639

[51] Int. Cl.$^6$ ............ C12Q 1/68; G01N 33/53; G01N 33/566; C07F 15/00
[52] U.S. Cl. ............ 435/6; 435/7.1; 435/7.5; 436/84; 436/501; 556/136
[58] Field of Search ............ 435/6, 7.1, 7.5, 435/975; 436/84, 501, 513, 800; 556/136

[56] References Cited

U.S. PATENT DOCUMENTS

| | | | |
|---|---|---|---|
| 4,358,535 | 11/1982 | Falkow et al. | 435/6 |
| 4,376,165 | 3/1983 | Hornby et al. | 435/188 |
| 4,490,543 | 12/1984 | Bergquist et al. | 549/212 |
| 4,581,333 | 4/1986 | Kourilsky et al. | 435/6 |
| 4,584,367 | 4/1986 | Matsuo et al. | 534/634 |
| 4,687,732 | 8/1987 | Ward et al. | 435/6 |
| 4,711,955 | 12/1987 | Ward et al. | 536/25.32 |
| 5,053,226 | 10/1991 | Rosenblum et al. | 424/78.31 |
| 5,175,269 | 12/1992 | Stavrianopoulos | 536/26.13 |
| 5,241,060 | 8/1993 | Engelhardt et al. | 536/25.32 |
| 5,279,656 | 1/1994 | Kenyon et al. | 106/31.43 |
| 5,328,824 | 7/1994 | Ward et al. | 435/6 |

OTHER PUBLICATIONS

A. van Belkum, et al., "Non–Isotopic Labeling of DNA by Newly Developed Hapten–Containing Platinum Compounds", *BioTechniques*, 16(1): 148–152 (1994).

A. van Belkum, et al., "Application of a New, Universal DNA Labeling System in the PCR Mediated Diagnoses of *Chlamydia Trachomatis* and Human Papillomavirus Type 16 Infection in Cervical Smears", *Journal of Virological Methods*, 45: 189–200 (1993).

N.P. Johnson, et al., "Structures of the Adducts Formed Between [Pt(dien)Cl]Cl and DNA in vitro", *Nucleic Acids Research*, 10(17): 5255–5271 (1982).

Jean–Pierre Macquet, et al., "A Circular Dichroism Study of DNA–Platinum Complexes", *Eur. J. Biochem*, 83: 375–387 (1978).

Jan Reedijk, "The Relevance of Hydrogen Bonding in the Mechanism of Action of Platinum Antitumor Compounds", *Inorganica Chimica Acta*, 198–200: 873–881 (1992).

J.G.J. Bauman, et al., "Cytochemical Hybridization with Fluorochrome–Labeled RNA", *The Journal of Histochemistry and Cytochemistry*, 29(2): 238–246 (1981).

Therald Moeller, "Ligand Substitution or Exchange, in 4–Coordinate, Square–Planar Complexes", pp. 714–716 in Inorganic Chemistry: A Modern Introduction, John Wiley & Sons, New York (1982).

J.G.J. Bauman, et al., "Rapid and High Resolution Detection of in situ Hybridisation to Polytene Chromosomes Using Fluorochrome–Labeled RNA", *Chromosoma (Berl.)*, 84: 1–18 (1981).

(List continued on next page.)

*Primary Examiner*—Nancy Degen
*Assistant Examiner*—William Sandals
*Attorney, Agent, or Firm*—Hoffmann & Baron, LLP

[57] ABSTRACT

The invention provides platinum-based probe compounds having the structure:

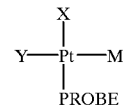

wherein: Pt is a platinum atom, PROBE is a probe biomolecule for associating to a target biomolecule, M is a detectable marker moiety, and X and Y are stabilizing substituents. Also provided are platinum-based labeling compounds having the structure:

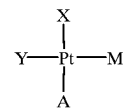

wherein: Pt is a platinum atom, M is a detectable marker moiety, A is a displaceable leaving group, and X and Y are stabilizing substituents. The invention further provides platinum-based linker compounds having the structure:

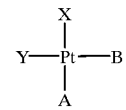

wherein: Pt is a platinum atom, A and B are the same or different reactive moieties, and X and Y are stabilizing substituents. Other $Pt^{II}$ and $Pt^{IV}$ compounds are also provided. Moreover, the invention provides methods for the preparation and use of these compounds, as well as diagnostic kits which contain the compounds.

15 Claims, No Drawings

OTHER PUBLICATIONS

Jan Reedijk, "The Mechanism of Action of Platinum Anti–Tumor Drugs", *Pure & Appl. Chem.*, 59(2): 181–192 (1987).

Alan Eastman, "The Formation, Isolation and Characterization of DNA Adducts Produced by Anticancer Platinum Complexes", *Pharmac. Ther.*, 34:155–166 (1987).

Susan J. Berners–Price, et al., "Stereospecific Hydrogen–Bonding in Mononucleotide Adducts of Platinum Anticancer Complexes in Aqueous Solution", *J. Am. Chem. Soc.*, 115(19):8649–8659 (1993).

*Gordon L. Johnson, "63. cis–Dichloro(ethylenediamine)–Platinum(II)", *Inorganic Syntheses,* (publication data unknown), pp. 242–244.

*George B. Kauffman, et al., "63. cis–And trans–Dichlorodiammine–Platinum(II)", *Inorganic Syntheses,* (publication data unknown), pp. 239–245.

*George W. Watt, et al., "Diethylenetriamine Complexes of Platinum(II) Halides", *Inorganic Chemistry,* 7(2): 335–338 (1968).

Ghebrehiwet et al. Reversible biotinylation of C1q with a cleavable biotinyl derivative Application in C1q receptor (C1qR) purification. J. Immunol. Methods vol. 110:251–260, Jun. 13, 1988.

Arpicco et al. New coupling reagents for the preparation of disulfide cross–linked conjugates with increase stability. Bioconjugate Chem. vol. 8(3):327–337, Jan. 10, 1997.

Bieniarz et al. Extended length heterobifunctional coupling agents for protein conjugations. Bioconjugate Chem. vol. 7:88–95, Feb. 8, 1996.

PLATINUM-CONTAINING COMPOUNDS, METHODS FOR THEIR PREPARATION AND APPLICATIONS THEREOF

CROSS REFERENCE TO RELATED APPLICATIONS

This application is a continuation of U.S. application Ser. No. 08/470,265, filed on Jun. 6, 1995, now U.S. Pat. No. 5,714,327, issued Feb. 3, 1998, which is a continuation-in-part of U.S. application Ser. No. 07/975,586, filed on Oct. 19, 1993, now U.S. Pat. No. 5,580,990, issued Dec. 3, 1996.

BACKGROUND OF THE INVENTION

The invention generally relates to platinum compounds, which may be used for detectably labeling biological target molecules. More particularly, the invention relates to platinum-based linker compounds, labeling compounds, and detectably labeled molecular probes and methods of using such compounds for the detection and localization of biological substances of interest.

Platinum (coordination) compounds have been considered interesting molecules for a very long time. For a review of some of these compounds and their uses we refer to Reedijk et al., *J. Struct. Bonding,* 67: 53–72 (1987). This article describes the anti-tumor compound cis-$Pt(NH_3)_2Cl_2$, which compound has a high affinity for certain biological or bio-organic molecules, including amongst others, proteins and DNA molecules. In particular, it appears that such compounds have a marked affinity for the $N^7$-nitrogen atom in the purine bases guanine and adenine, as well as for sulfur groups in macromolecules.

By dissociation of the two chlorine ligands in these compounds, two reactive sites arise, with which such platinum compounds can cross-link within or between molecules. For example, such compounds are known to cross-link between two neighboring guanine and/or adenine bases in the same or opposite DNA strands, thereby inhibiting the replication of the DNA molecules. The application of cis-platinum (cisplatin) as an anti-tumor drug (cytostaticum) is based on this mechanism.

Other applications of the cross-linking capacity of such compounds have been explored. For example, U.S. Pat. No. 4,490,543 discloses platinum-based radiation sensitizers which are said to be derivatives of cisplatin. These sensitizers contain two reactive groups and, accordingly, cross-link biological molecules such as DNA.

In contrast, monochlorinated platinum compounds like Pt(dien)Cl appear to keep their DNA affinity, but they do not form cross-links and interfere only slightly with the base pairing of complementary DNA strands. As such, these compounds have no anti-tumor activity.

According to U.S. Pat. No. 4,711,955, non-radioactive nucleic acid labeling techniques are preferred in present medical-biological practice, especially diagnostic practice. The presently applied known non-radioactive labeling techniques for DNA and RNA are globally to be divided in two categories:

1. Labeling which proceeds via enzymatic or organic synthetic routes; for instance biotin, bromodeoxyuridine (BrdU), digoxigenin, fluorescein and peroxidase;
2. Labeling by direct chemical coupling, like photobiotin, AAF, mercury, and sulfone groups. The '955 document discloses one such labeling method, but does not provide any information concerning use of platinum-based compounds for this purpose.

Application of detectable labels to biomolecules has been typically accompanied by a number of problems. Such problems are a result of several factors, including the complexity of previous labeling procedures, limitations on the length of the synthetic oligonucleotides which have been desired to be labeled, the necessity of using health-injuring compounds, and a lack of stability of the label when it has been bound to the nucleic acid.

Given these limitations in the conventional methods of labeling bio-organic target molecules, it is desirable to provide labeling method which overcomes these problems. Probe compounds are desired which can accommodate ready attachment of a large variety of detectable markers. It is also desirable to provide detectably labeled probe compounds which can quickly and easily identify specific bio-organic target molecules such as nucleic acids and proteins. In addition, it would be desirable to provide detectably-labeled probe compounds which would specifically interact with particular bio-organic target molecules, but which do not substantially interfere with their function.

The present invention now provides platinum-containing compounds, in the application of which the above-mentioned disadvantages are effectively removed.

SUMMARY OF THE INVENTION

The present invention provides platinum-based compounds which are controllably and substantially irreversibly reactive with biological molecules, including methods of making such compounds and methods for their use. The invention further provides platinum-based compounds useful for detecting the presence of biological target molecules, as well as methods for employing such compounds. The invention further includes diagnostic kits containing platinum-based compounds of the invention which permit the labeling of biomolecules, and the detection of target biomolecules in a variety of testable systems.

In a preferred embodiment, the invention provides detectable probe compounds having the structure:

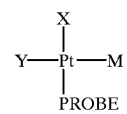

wherein:

Pt is a platinum atom,

PROBE is a probe biomolecule for associating to a target biomolecule,

M is a detectable marker moiety, and

X and Y are stabilizing substituents.

Preferably, the PROBE moiety is a biomolecule such as a nucleic acid, a protein, or a lipid. More preferably, the PROBE moiety is a biomolecule selected from among nucleotides, nucleosides, modified nucleotides, modified nucleosides, oligonucleotides, polynucleotides, amino acids, modified amino acids, oligopeptides, polypeptides, proteins, glycoproteins, lipoproteins, steroids, fatty acids, and the like.

The detectable marker moiety (M) may include any moiety known in the art which is detectable, either directly, e.g., a fluorescent compound, or indirectly, e.g., an enzyme which cause a color change in a medium. Preferably, the detectable marker moiety is selected from among radioactive labels, enzymes, specific binding pair components, colloidal dye substances, fluorochromes, chromogens, reducing substances, colored latex sols, digoxigenin, metal sols, particulate sols, dansyl lysine, antibodies, protein A, protein G, and the like. Still more preferably, the detectable marker moiety is a fluorescent group chosen from among compounds such as fluoresceins, eosins, trisulfonylpyrenes, rhodamines, digoxigenins, 4,4-difluoro-4-bora-3a,4a-diaza-s-indacenes, and derivatives thereof. Other more preferred M moieties include binding pair components chosen from among biotins, iminobiotins, avidins, streptavidins, biocytins, and derivatives thereof.

The stabilizing substituents X and Y may be the same or different, and are substantially unreactive with biomolecules of interest. In a preferred embodiment, X and Y are interconnected, forming a stabilizing bridge moiety. Preferred stabilizing bridge moieties include aliphatic diamines, more preferably aliphatic diamines having between 2 and 6 carbon atoms. A highly preferred stabilizing bridge moiety is ethylenediamine.

In another preferred embodiment, the invention provides detectable labeling compounds having the structure:

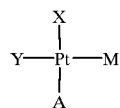

wherein:

Pt is a platinum atom,

M is a detectable marker moiety,

A is a displaceable leaving group, and

X and Y are stabilizing substituents.

In this embodiment, the detectable marker moiety M and the stabilizing substituents X and Y are as defined above. The displaceable leaving group A may be any moiety which is displaced, readily and in an at least substantially irreversible manner, by a biomolecule such as a nucleic acid or a protein. Preferred leaving ligands include compounds having the structure of either Formula 1 or Formula 2, include halogens, $SO_3^{2-}$, $NO_3^-$, $PO_4^{3-}$, $CO_3^{2-}$, and analogs like ethylnitrate; phosphonates, carboxylates, oxalates, citrates and derivatives thereof; $H_2O$, ROH and $RO^-$, in which R is an organic residual group and substituted sulfoxides $R^1R^2SO$, in which $R^1$ and $R^2$, whether or not identical to each other, represent organic residual groups. More preferred displaceable leaving groups include $(CH_3)_2SO$, $H_2O$ and Cl.

The invention also provides platinum-based binding substances having the structure:

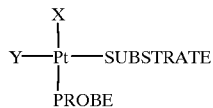

wherein:

Pt is a platinum atom,

PROBE is a biomolecule as defined previously for associating to a target biomolecule, SUBSTRATE is a substantially solid material, and X and Y are stabilizing substituents as defined previously.

In this embodiment, the invention provides probe molecules which have been linked to and substantially immobilized on a substrate or surface. Preferably, such substrates or surfaces may include gels, resins, beads, nitrocellulose, nylon filters, microtiter plates, culture flasks, and the like. The PROBE moiety is preferably as defined above. The stabilizing substituents X and Y are preferably as defined above.

In another embodiment, the invention provides a platinum-based linker compound having the structure:

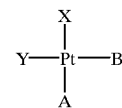

wherein:

Pt is a platinum atom,

A and B are the same or different reactive moieties, and

X and Y are stabilizing substituents.

In this embodiment, the reactive moieties A and B are reactive with biomolecules and/or substrate materials. Typically, A and B are electronegative moieties. The linker compounds of the invention may be employed to controllably react with marker moieties and probe moieties to provide the detectably labeled probes and labeling compounds of the invention, as described elsewhere herein.

In addition, the invention provides methods of using the compounds of the invention for binding to and/or detectably labeling biomolecules of interest, as well as detecting the presence or absence of target biomolecules in specific testable systems.

Thus, the invention provides a method for detecting a biological target molecule by means of detectably labeled probe compounds. In this approach, the method includes:

providing to a testable system a platinum-based detectably labeled probe as described above, and detecting a target biomolecule by determining the extent of association or binding between the detectably labeled probe and the target biomolecule. In this method, the detectably labeled probe binds at least selectively or preferentially to the target biomolecule. In preferred embodiments, however, the detectably labeled probe binds specifically, more preferably uniquely, to the target biomolecule. A highly preferred embodiment involves the induction and detection of in situ hybridization between a detectably labeled nucleic acid of the invention and a target nucleic acid.

The invention also provides a method for selectively binding a target biomolecule. This method includes:

contacting a sample, which contains a target biomolecule, with a platinum-based binding substance as described elsewhere herein. In this embodiment, the platinum-based binding substance, which is linked to a substantially solid substrate or surface, possesses a probe molecule associates with or binds to a target biomolecule. Thus, the invention provides, in a preferred situation, a method for specifically binding a target molecule in a quantitative or semi-quantitative assay such as an ELISA. Alternatively, the invention provides a method for separating a target molecule from a sample, such as for purification of the target substance.

The invention further provides diagnostic kits for detecting determining or localizing biological substances of interest. In one embodiment the diagnostic kit includes (a) a detectable probe compound having the structure:

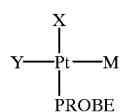

wherein:
Pt is a platinum atom,
PROBE is a probe biomolecule for associating to a target biomolecule,
M is a detectable marker moiety, and
X and Y are stabilizing substituents; and
(b) a container.

In another embodiment, the diagnostic kit of the invention includes:
(a) a platinum-based linker compound having the structure:

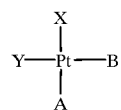

wherein:
Pt is a platinum atom,
A and B are the same or different reactive moieties, and
X and Y are stabilizing substituents; and
(b) a detectable marker moiety
(c) a container.

In still another embodiment, the invention provides a diagnostic kit which includes:
(a) a platinum-based linker compound having the structure:

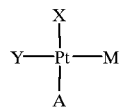

wherein:
Pt is a platinum atom,
A is a reactive moiety,
M is a detectable marker moiety, and
X and Y are stabilizing substituents; and
(b) a container.

In still another embodiment, the invention provides a method for the preparation of a platinum-based linker compound for attachment to biomolecules. In this embodiment, the method includes:
modifying a starting material, which includes a compound of the structure:

wherein C represents an electronegative reactive moiety, to produce a platinum-based linker compound of the structure:

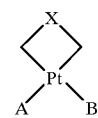

wherein X represents any stabilizing bridge and wherein A and B represent the same or different reactive moieties. Preferably, X represents a polyamine, more preferably, an aliphatic diamine, still more preferably, an aliphatic diamine having 2–6 carbon atoms, and most preferably, an ethylenediamine group. The reactive moieties A and B are preferably the same. Moreover, A and B are preferably selected from among halogens, $NO_3^-$, and $SO_3^-$. Preferably the C moiety is selected from among halogens, $NO_3^-$, and $SO_3^-$.

The invention further provides a method for the preparation of linkers for attachment to biomolecules, in which the method includes;
reacting a starting material of the structure:

wherein C represents a halogen, with ethylenediamine, and
reacting the resulting compound with $AgNO_3$, to provide a linker comprises a platinum compound of the formula:

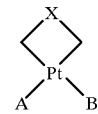

wherein X represents an ethylenediamine group and wherein A and B represent $NO_3^-$.

Further, the invention provides a method for preparing a platinum-based labeling compound, in which the method includes:
modifying a compound of the structure:

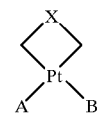

wherein X represents any stabilizing bridge and wherein A and B represent the same or different reactive moieties, to produce a platinum-based labeling compound of the structure:

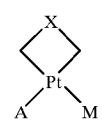

wherein M is a detectable marker moiety.

The invention further provides a method for detectably labeling a biomolecule. Here, the method includes:
reacting a platinum-based labeling compound of the formula:

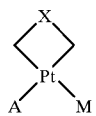

with a biomolecule, whereby, as a result of said reacting, the A group of the platinum-based labeling compound is replaced by the biomolecule. Preferably, the biomolecule is selected from among proteins, peptides, DNA molecules, and RNA molecules.

The invention also provides a diagnostic kit for detecting biological substances of interest, in which the kit includes:

a platinum-based linker compound of the formula

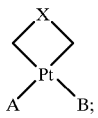

a detectable marker moiety; and a container. The diagnostic is kit preferably further includes additional detection means such as other marker moieties.

The invention still further provides a diagnostic kit for detecting biological substances of interest, in which the kit includes a platinum-based labeling compound of the formula:

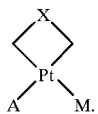

In this embodiment, the diagnostic kit preferably also includes additional detection means such as one or more other marker moieties.

Still further, the invention provides a diagnostic kit for detecting biological substances of interest, wherein the kit includes a detectably labeled biomolecule of the formula:

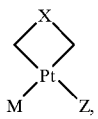

wherein X represents a stabilizing bridge, M represents a detectable marker moiety, and Z represents a biomolecule. The diagnostic kit preferably further includes additional detection means such as other detectable marker moieties.

Also provided by the invention is a detectably labeled biomolecule having the structure:

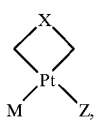

wherein X represents any stabilizing bridge, wherein M represents a detectable marker moiety, and wherein Z represents a biomolecule.

These and other advantages of the present invention will be appreciated from the detailed description and examples which are set forth herein. The detailed description and examples enhance the understanding of the invention, but are not intended to limit the scope of the invention.

DETAILED DESCRIPTION OF THE INVENTION

A new and different use of platinum (coordination) compounds has now been developed in which a platinum compound having only a single reactive moiety (also referred to herein as a "leaving group"), and at least one detectable marker moiety, such as a fluorescein moiety, are employed to bind (non-covalently) to a bio-organic target molecule, such as at the $N^7$ position of a guanine residue in a nucleic acid. Because these compounds have only one leaving group, they efficiently and irreversibly bind to target molecules without cross-linking, providing an exquisite new means by which to detectably label bio-organic molecules.

Thus, the present invention provides platinum-containing compounds which are highly suited for use in detectably labeling bio-organic target molecules, improved methods of preparing platinum compounds which are suitable for use in such labeling substances, improved methods of preparing labeled substances, methods of using such substances in detectably labeling and preferentially binding biomolecules, and diagnostic test kits for detecting biomolecules.

In a preferred embodiment, the invention provides detectable probe compounds having the structure:

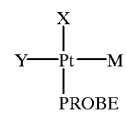

wherein:

Pt is a platinum atom,

PROBE is a probe biomolecule for associating to a target biomolecule,

M is a detectable marker moiety, and

X and Y are stabilizing substituents.

Preferably, the PROBE moiety in the compounds of the invention is a biomolecule such as a nucleic acid, a protein, or a lipid. More preferably, the PROBE moiety is a biomolecule selected from among nucleotides, nucleosides, modified nucleotides, modified nucleosides, oligonucleotides, polynucleotides, amino acids, modified amino acids, oligopeptides, polypeptides, proteins, glycoproteins, lipoproteins, steroids, fatty acids, and the like.

Bio-organic molecules which contain an S (sulfur) or an N (nitrogen) can be labeled with the platinum compounds of the present invention. A very suitable bio-organic molecule to be labeled with the labeling substance according to the invention is natural, modified, synthetic, or recombinant nucleic acid (e.g., nucleotides, oligonucleotides, DNA, RNA, homoduplexes, heteroduplexes, or multiplexes). However, amino acids, modified amino acids, oligopeptides, polypeptides, proteins, enzymes, glycoproteins, lipoproteins, and other peptide-based molecules whether synthetic or naturally-occurring, may be detectably labeled according to the invention. In addition, other bio-organic molecules, such as lipids, fatty acids, and steroids, can also be labeled with the labeling substances according to the invention. This list of biomolecules is intended to be illustrative of the invention and non-limiting.

The platinum-based compounds of the invention can be labeled with any suitable detectable label or marker compound known in the art. The labels may be detectable by direct or indirect methods such as those known in the art. These marker moieties (M) may be radioactive labels, enzymes (which need reaction with a substrate to be detected), specific binding pair components (e.g., avidin, streptavidin, biotin, biocytin, iminobiotin), colloidal dye substances, fluorochromes (fluorescein, rhodamine, etc.), reducing substances (eosin, erythrosin, etc.), (colored) latex sols, metal sols or other particulate sols (selenium, carbon and the like), dansyl lysine, antibodies, protein A, protein G, electron dense materials, chromophores, etc.

As the detectable marker group M in the compounds having Formula 1 or 2, a fluorescent group is generally preferred. More preferably, the fluorescent groups is selected from among fluoresceins, eosins, trisulfonylpyrenes, rhodamines, digoxigenins, 4,4-difluoro-4-bora-3a,4a-diaza-s-indacenes, and derivatives thereof. Especially preferred M groups include fluorescein isothiocyanate (FITC) or tetramethyl rhodamine isothiocyanate (TRITC).

One or more of these markers M may be attached to the platinum compounds either directly or through spacer arms (preferably polylysine). Spacer arms are particularly desirable in cases in which steric hindrances due to molecular dimension or interaction would otherwise inhibit or prevent binding. Because the labeling of nucleic acids and proteins is so easy using the compounds of the invention, it is possible to sell the linker-label compounds separately in a kit so that any user can produce the labeled substances easily, or can attach by the same procedure many different markers of choice to the substances. This allows for multiple detections in one assay.

The stabilizing substituents in the platinum-based compounds of the invention include moieties which are at least substantially stable or unreactive under conditions of storage and/or use of the compounds. The stabilizing substituents may be same or different from one another, and may be selected by the artisan depending upon the desired conditions of use since these substituents may affect the physical and/or chemical properties of the compounds, e.g., solubility, hydrophobicity/hydrophilicity, etc. In preferred embodiments, stabilizing substituents are interconnected, together constituting a stabilizing bridge moiety. A stabilizing bridge is, therefore, at least divalent, occupying two ligand sites with the platinum atom, but may be multivalent, occupying more than two such ligand sites. Preferred stabilizing bridges include aliphatic amine compounds. Divalent stabilizing bridges are preferred for use in the Pt(II)-based compounds of the invention. A preferred divalent stabilizing bridge is ethylenediamine (also abbreviated herein as "(en)"). Multivalent stabilizing bridges are preferred for use in the Pt(IV) compounds of the invention, although divalent stabilizing bridges and unbridged stabilizing substituents may also be employed alone or in combination. A preferred multivalent stabilizing bridge is diethylenetriamine (also known as "(dien)"), which can occupy three ligand sites on a Pt(IV) atom.

In another preferred embodiment, the invention provides detectable labeling compounds having the structure:

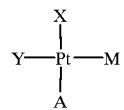

wherein:

Pt is a platinum atom,

M is a detectable marker moiety as defined previously,

A is a displaceable leaving group, and

X and Y are stabilizing substituents as defined previously.

The labeling compounds of this embodiment are reactive with biomolecules such as nucleic acids and proteins. The reaction of the labeling compound with a biomolecule is controllable and substantially irreversible, permitting the stable and detectable labeling of a variety of biological compounds. This reaction of the labeling compound with such a target molecule involves the displacement of the leaving group A to be replaced with a single linkage to the target molecule. Accordingly, the displaceable leaving group A may be any group which can be displaced by a biomolecule when the labeling compound and the biomolecule react with one another. In this way, the compounds of the invention can be employed to label biomolecules without inducing cross-linking within or between the biomolecules.

Leaving groups suitable for use in the compounds of the invention would include any group which would be replaced in favor of a bio-organic molecule of interest under appropriate conditions. For example, suitable leaving groups for the labeling of a nucleic acid would include groups which would permit a bond between the platinum atom and the nucleic acid to be formed under appropriate conditions. The selection of leaving groups, therefore, is within the discretion of the artisan with respect to the system in which the platinum compounds are to be employed and the target molecules which are to be labeled. The artisan would understand that a comparison of the electronegativities of the leaving group and the target molecule would be useful in selecting a leaving group for a particular application.

As leaving ligands, $(CH_3)_2SO$, $H_2O$ and $Cl$ are especially suitable according to the invention. Other leaving ligands suitable for use in compounds of the invention, including compounds having the structure of either Formula 1 or Formula 2, include halogens, $SO_3{}^{2-}$, $NO_3{}^-$, $PO_4{}^{3-}$, $CO_3{}^{2-}$, and analogs like ethylnitrate; phosphonates, carboxylates, oxalates, citrates and derivatives thereof; $H_2O$, ROH and $RO^-$, in which R is an organic residual group and substituted sulfoxides $R^1R^2SO$, in which $R^1$ and $R^2$, whether or not identical to each other, represent organic residual groups.

The invention also provides platinum-based binding substances having the structure:

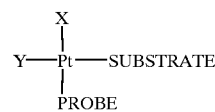

wherein:

Pt is a platinum atom,

PROBE is a biomolecule as defined previously for associating to a target biomolecule, SUBSTRATE is a substantially solid material, and X and Y are stabilizing substituents as defined previously.

In this embodiment, the invention provides probe molecules which have been linked to and substantially immobilized on a substrate or surface. Preferably, such substrates or surfaces may include gels, resins, beads, nitrocellulose, nylon filters, microtiter plates, culture flasks, and the like. Any suitable substantially solid material may be linked to a biomolecule according to this embodiment. Such bound biomolecules may be employed for the removal of specific target biomolecules from a test material. Thus, the invention provides compounds which enable the performance of solid phase diagnostic assays such as immunosorbent assays, as well as purification of target biomolecules and column chromatographic analyses. Other methods will present themselves to the skilled artisan in order to take advantage of the new and direct linking capacity of the compounds of the invention.

In another embodiment, the invention provides a platinum-based linker compound having the structure:

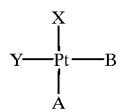

wherein:

Pt is a platinum atom,

A and B are the same or different reactive moieties, and

X and Y are stabilizing substituents as defined previously.

In this embodiment, the reactive moieties A and B are reactive with biomolecules and/or substrate materials. Typically, A and B are electronegative moieties. The linker compounds of the invention may be employed to controllably react with marker moieties and probe moieties to provide the detectably labeled probes and labeling compounds of the invention, as described elsewhere herein. Preferred reactive moieties include those moieties defined elsewhere herein as leaving ligands.

More generally, the invention provides, inter alia, platinum-based marker compounds having the general formula $\{Pt^{II}(w)(x)(y)(z)\}$ or $\{Pt^{IV}(u)(v)(w)(x)(y)(z)\}$:

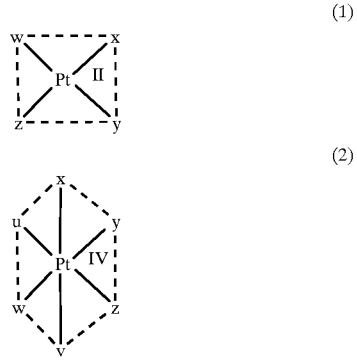

In Formulas 1 and 2, u, v, w, x, y and z represent ligands to the platinum atom. Formula 1 represents a tetravalent platinum compound having a square planar, tetragonal structure. Formula 2 represents a hexavalent compound having octahedral structure. In these structures, no more than one ligand is a leaving group, characterized by its ability to be substituted or replaced by a biomolecule of interest. At least one of the ligands represents a detectable marker group. The remaining ligands are stabilizing substituents, and may be the same as or different from one another. Two or more of the ligand sites may be interconnected by the stabilizing ligand(s), preferably covalently, to form a stabilizing bridge as desired. Preferred interconnected groups include aliphatic polyamines. A preferred interconnected group of ligands is ethylenediamine ($-NH_2-CH_2-CH_2-H_2N-$) which can occupy two ligand sites when bound to the platinum atom. Ethylenediamine is abbreviated herein as "en".

On the one side, these compounds are provided with a directly or indirectly detectable marker group, as for instance a hapten, fluorescein or rhodamine. On the other side, the compounds are provided with a suitable leaving group. Such compounds are provided as especially suitable and novel DNA labels. These platinum-based detectably labeled compounds of the invention are generally designated herein as "PtM" compounds, wherein "Pt" stands for platinum and "M" stands for a detectable marker group. A preferred PtM marker compound according to the invention is $\{Pt(ethylenediamine)(Me_2SO)(fluorescein-NH(CS)-NHCH_3)\}$, (hereinafter also designated "PtF", wherein F stands for a fluorescein moiety).

Further, the invention comprises a process for the preparation of Pt-containing compounds according to the invention with the formula $\{Pt^{II}(w)(x)(y)(z)\}$ or $\{Pt^{IV}(u)(v)(w)(x)(y)(z)\}$ with the structural Formula 1 or 2, respectively, in which u, v, w, x, y and z have the aforementioned meanings.

A preferred compound according to the invention, to wit PtF, is prepared by conversion of fluorescein-N=C=S by reacting this compound with $CH_3NH_2$ in water, after which the mentioned fluorescein-NH(CS)-NHCH$_3$ is precipitated from the solution by acidifying to a pH of 2–3, after which the precipitate obtained is suspended in water and the pH of the suspension is brought to a value of 10–11 by addition of a base, providing a bright yellow solution, to which solution $\{Pt(ethylenediamine)(Me_2SO)Cl\}$ in water is added and the reaction mixture is stirred at room temperature in the dark, after which the non-reacted fluorescein-NH(CS)NHCH$_3$ is precipitated by acidification and filtered and finally the filtrate is freeze-dried yielding $\{Pt(ethylenediamine)(Me_2SO)(fluorescein-NH(CS)NHCH_3)\}(PtF)$.

The compounds of the invention adhere spontaneously and irreversibly to DNA in aqueous media. Further, the thus labeled DNA may be separated from the redundant, unbound compound by alcohol precipitation. An important advantage is that the thus labeled DNA may be detected immediately after hybridization, such as by means of a fluorescence microscope or indirectly with one of the known immunohistochemical staining techniques depending on the label which is employed.

Advantages of the present platinum-containing compounds include, inter alia:

1. Direct and almost instantaneous labeling of macromolecules without necessity of enzymatic or organosynthetic procedures;
2. One-step purification of labeled molecules by means of a simple routine technique;
3. Direct and/or indirect detection of labeled molecules by way of almost all known (microscopic) techniques.

Accordingly, the invention further includes a method for the diagnosis of viral, bacterial, or parasitic infection, detection of genetic deviation, or detection of gene expression. In this embodiment, the invention includes detecting a detectably labeled protein or nucleic acid specific for a viral, bacterial, or parasitic infection, genetic deviation, or gene expression, wherein protein or nucleic acid has been detectably labeled with a platinum-based labeling compound.

Moreover, the invention provides a method of detectably labeling a nucleic acid or protein molecule, including replacing the leaving group in a platinum-based compound of Formula 1 or 2 with a nucleic acid or protein molecule. The invention also includes a detectable probe molecule, including a nucleic acid or protein which has been detectably labeled with at least one platinum-based compound of Formula 1 or 2. Preferred detectable probes include labeled nucleic acid molecules. A highly preferred such nucleic acid probe is a nucleic acid which has been labeled with {Pt(ethylenediamine)(Me$_2$SO)(fluorescein-NH(CS)—NHCH$_3$)}.

The invention also includes a method of detecting a specific nucleic acid sequence, wherein the method includes:

(a) hybridizing a nucleic acid probe labeled with a compound of Formula 1 or 2 with a nucleic acid to be detected; and (b) detecting the nucleic acid probe.

In addition, the invention includes a diagnostic kit for the detection of a specific nucleic acid sequence. In this embodiment, the kit includes a nucleic acid probe labeled with a compound of Formula 1 or 2, enabling the detection of specific nucleic acid sequences.

As a further advantage, it may be mentioned that, for specific purposes (for instance, extra sensitive in situ hybridization of RNA), a radioactively labeled platinum (PtM) compound according to the invention (i.e., wherein the "M" group contains a radioisotope such as $^{14}$C or $^{35}$S) may be applied for simple and fast (non-enzymatic) labeling of probes, followed by direct detection by means of autoradiography.

Another important new application of the probes labeled with the present compounds is the detection of in situ hybridization in the electron microscope. In this method, the high mass of the platinum atom in the compound according to the invention compensates for a direct probe-specific local increase of the electron density.

Furthermore, in addition to the advantages described above, another advantage of the platinum compounds of the invention is that they can be detected more or less directly by using the platinum as a nucleus for depositing silver or other metal crystals.

In the labeling of nucleic acid molecules, the platinum compounds of the invention bind very easily (non-covalently) to the N$^7$ position of purine residues, preferentially binding to guanine. In this way, DNA or RNA molecules (single stranded or otherwise), can be easily detected, but the method of the invention also allows for the production of probes for hybridization techniques wherein unlabeled DNA/RNA molecules hybridize to the labeled probe. The platinum compounds hardly interfere with the hybridization, if at all. This technique also obviates the necessity to use modified nucleotides in preparing nucleic acid probes since it permits such probes to be prepared in advance and then labeled. Nonetheless, these compounds can be used to label nucleotides for subsequent incorporation into nucleic acids or for other purposes.

The platinum-based compounds of the invention may also be used to detectably label any of a variety of complementary members of specific binding pairs. Such specific binding pairs include antibody-antigen, antibody-hapten, complementary nucleic acids, avidin-biotin, streptavidin-biotin, protein subunit-protein subunit, enzyme-substrate, enzyme-enzyme, enzyme-cofactor, enzyme-inhibitor, receptor-agonist, receptor-antagonist, saccharide-lectin, glycoprotein-lectin, glycolipid-lectin, and the like.

In one embodiment, one member of a binding pair is detectably labeled using a platinum-based labeling compound, while the complementary member of the pair is the target which is to be detected. For example, if a receptor is desired to be detected, a ligand (e.g., agonist) for the receptor is attached to the platinum compound which itself has a detectable label. When the ligand binds to the receptor, the receptor is effectively detectable. In another embodiment, the detectable label is a member of a binding pair, such as biotin. In this case, when the platinum compound binds to a target molecule, detection is accomplished by means of contacting the label (biotin) with a detectably-labeled complementary member of the binding pair, for example, fluorescent-labeled avidin. In still another embodiment, each member of a binding pair can be separately labeled, e.g., with different markers to identify the presence of binding under particular conditions. Other examples of uses of the compounds of the invention will present themselves to the skilled artisan.

Nucleotides modified in accordance with the practices of this invention, oligo- and polynucleotides into which the modified nucleotides have been incorporated, or oligo- and polynucleotides that have been directly modified using these novel platinum compounds, may be used as probes in biomedical research, clinical diagnostics, and recombinant DNA technology.

Another utility of the platinum compounds of the invention is based upon their ability to form stable complexes with polypeptides which, in turn, can be detected either by means of detectable moieties which are attached to, or which interact with, the polypeptide. Thus, platinum compounds which have polypeptides as marker moieties (enabling indirect detection) may be used as labeling compounds to label target biomolecules such as nucleic acids. Some uses according to this embodiment include detecting and identifying nucleic acid-containing etiological agents, e.g., bacteria and viruses; screening bacteria for antibiotic resistance; screening animals and persons for genetic disorders in relation to pharmaceutical effects; diagnosing genetic disorders, e.g., trisomy 21, sickle cell anemia; chromosomal karyotyping; and identifying tumor cells.

The novel compounds according to the invention are especially suitable for viral diagnostic purposes, bacterial diagnostic purposes, detection of genetic deviations, detection of gene expression, etc.

A number of viruses are known which cannot, or can only with great difficulty, be brought into culture, or for which the serological diagnostic methods are extremely complicated, or which are very labile outside the body, and are, therefore, unsuitable in contamination tests.

With some of these viruses diagnosis may, moreover, be hindered by the necessity of differentiation between an acute stage of the illness, carrier status, or virus genome insertion in the human DNA. Some viruses have, in addition, serious pathogenic effects and are related with the development of malignant tumors. The accurate detection of these viruses and the correlation with a clinical follow-up of patients is, therefore, an important matter.

Detection methods using labeled DNA or RNA probes appear to be able to solve these problems. For example, virus strains or subtypes may, in principle, be distinguished from each other by DNA/RNA probes. Much progress has been made in the diagnosis of both DNA and RNA viruses. The advantage of these methods is that immediately the patient material (smears, samples of blister, nose and other fluids, tissue sections, etc.) may be tested on the presence of virus DNA/RNA. Also, retrospective studies have already provided important information about viral causes of mortality, etc.

Subsequently, the invention extends to a diagnostic kit for use in the detection of viruses, bacteria, parasites, genetic deviations, and gene expression. In one embodiment, the kit includes a Pt-containing compound according to the invention and a container, such as a reaction vial in which a biological compound may be labeled. In another embodiment, the kit may include a biological compound which has been labeled in accordance with the invention, and a container suitable for using the labeled compound to detect a target molecule. In the kit, other components may be included, such as internal positive and negative control compounds, buffers, salts, preservatives, etc.

The invention also provides intermediate platinum-containing compounds and methods of making such compounds. These compounds include symmetrical platinum(II) compounds having two electronegative groups. Typically, these compounds have the structure Pt(en)E$_2$, in which "(en)" represents an ethylenediamine group occupying two of the ligand sites, and "E" represents electronegative moieties which occupy the remaining two ligand sites. Comparable structures may be derived using platinum(IV). Preferred intermediate compounds may be made by reacting ethylenediamine with PtE$_4$, to yield Pt(en)E$_2$.

The electronegative E groups may be selected from among the leaving groups identified elsewhere herein. Preferred E groups include halides, —NO$_3$, and —SO$_3$. A particularly preferred intermediate compound of the invention is platinum(ethylenediamine)(NO$_3$)$_2$.

We have now found a very simple and reliable method of producing novel symmetrical platinum-based linkers through selection of suitable starting compounds of the formula PtE$_4$, wherein E is an electronegative group, preferably a halogen, NO$_3^-$, or SO$_3^-$. The reaction, of these starting compounds with ethylenediamine is very simple and efficient, as described in the Examples provided hereinbelow. Moreover, this reaction leads to very suitable symmetric intermediate compounds for producing labeled substances. The advantages of working with these starting compounds for producing labeled substances have never been disclosed and these starting compounds have never been used for this purpose.

A major advantage of using the compounds of the present invention is that, when a stabilizing bridge for the resulting platinum compound has to be attached, no blocking reagents are needed. Another advantage is that the resulting intermediate compounds can again be labeled without the use of blocking agents. Therefore, steps involved in the removal of blocking agents can be eliminated completely. Furthermore, the yields of these reactions are very high. Another advantage of the use of these symmetrical starting compounds is that no mixtures of different resulting compounds can be formed, which might otherwise interfere with the subsequent reaction and reduce yield or require extra separation steps.

A very suitable novel intermediate or linking compound according to the invention is Pt(en)(NO$_3$)$_2$ or platinum(II) (ethylenediamine) (NO$_3$)$_2$. It has now been found that this substance can very easily be provided with a single suitable labeling group, resulting in a labeling substance which can still, through substitution of the remaining NO$_3$ group, be linked to a bio-organic molecule to be labeled or detected. This reaction proceeds much faster than with previously known platinum compounds. Furthermore, the methods for producing this compound and the resulting labeled compound do not involve highly toxic substances such as dimethyl sulfoxide (DMSO).

Intermediate platinum compounds according to the invention may be prepared by a process which involves:

(a) reacting a compound having the structure:

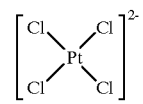

with potassium iodide (KI) in a suitable solvent under suitable conditions so as to form a iodated platinum compound having the structure:

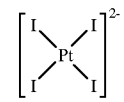

(b) reacting the iodated platinum compound obtained in step (a) with ethylenediamine in a suitable solvent so as to form a diethyleneamine iodated platinum compound and represented by the formula Pt(en)I$_2$ and having the structure:

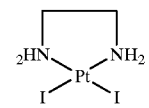

(c) reacting the compound obtained in step (b) with silver nitrate (AgNO$_3$), the reaction being carried out in a suitable solvent, under suitable conditions so as to form a compound having the structure:

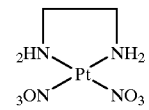

(d) reacting the compound obtained in step (c) with potassium chloride (KCl) in a suitable solvent under suitable conditions so as to form a compound having the structure:

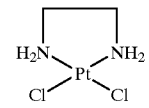

(e) reacting the compound obtained from step (d) with AgNO$_3$ in a suitable solvent, under suitable conditions so as to form a compound having the structure:

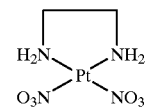

(f) recovering the compound obtained from step (e) as a modified platinum starting compound for the synthesis of marker-bound Pt-containing compounds for use in detectably labeling biological target molecules.

The intermediate compounds can also be employed as linker or bridge moieties according to the invention. In one embodiment, the intermediate compound is attached to a detectable label, to provide the detectable marker compounds of the invention such as Pt(en)(M)(E), in which M is a marker moiety and E is a leaving group. In another embodiment, the linker compound is attached to a substrate or surface, to provide an immobilized platinum-containing material, such as Pt(en)(Substrate)(E), which can be used to bind biomolecules in non-specific fashion.

Other advantages and embodiments of the invention will become clear from the following experimental part. The invention is now further elucidated with reference to the following illustrative and non-limiting examples.

EXAMPLE 1
Preparation of Platinum Ethylenediamine Nitrate

Platinum ethylenediamine($NO_3$)$_2$ (also referred to herein as "Pt(en)($NO_3$)$_2$") was prepared according to the following method. All reactions were performed in the dark.

One (1) gram of potassium tetrachloroplatinate (II), ($K_2PtCl_4$) (2.4 mmol, Sigma) was dissolved in 50 mL filtered water and stirred at room temperature. Ten (10) equivalents of potassium iodide (KI) (24 mmol, 3.999 g, Sigma) were added. The color of the solution immediately turned from orange into dark red ($K_2PtI_4$). The solution was stirred for 5 minutes.

Ethylenediamine (2.4 mmol, 160.8743 µL, Merck (1 L=0.9 kg)) was diluted in 5 mL filtered water, and 1 equivalent of ethylenediamine was added very slowly to the platinum solution. This solution was mixed for 1 hour at room temperature. A yellow/brown precipitate, Pt(en)$I_2$, was formed and the liquid standing above was clear.

The reaction mixture was filtered through a 1.0 µm membrane filter (Schleicher & Schuell, Dassel, Germany). The precipitate was washed with MILLIPORE filtered water, ethanol, and diethylether (in that order). The product Pt(en)$I_2$ was dried for 4 hours in a vacuum drying oven at 37° C.

The dried Pt(en)$I_2$(~1.07 g) was suspended in a mixture of 45 mL filtered water/5 mL acetone. The solution was cloudy. Silver nitrate ($AgNO_3$, 1.95 equiv., m.w.=169.9, Sigma) was added, and the reaction was stirred overnight at room temperature.

The reaction mixture was filtered through a 1.0 µm membrane filter. The precipitate was silver iodide (AgI), and the filtrate, containing Pt(en)($NO_3$)$_2$, was clear.

To a 0.5 mL aliquot of the filtrate, an excess of KCl was added, ensuring that no white precipitate was formed immediately after the addition, but only a yellow precipitate. (NaCl may be used instead of KC1.) An excess of KCl was then added to the entire filtrate. After the yellow precipitate is formed, the solution was filtered and the precipitate (Pt(en)$Cl_2$) was washed with filtered water, ethanol, and diethylether, in that order.

The precipitate was dried for 4 hours in a vacuum drying oven at 37° C. The dry Pt(en)$Cl_2$ (m.w.=326.1) was suspended in 45 mL filtered water/5 mL acetone and the cloudy suspension was stirred. $AgNO_3$ was added (1.95 equiv.) and the solution was stirred overnight at room temperature. The color of the solution became white, due to the formation of AgCl.

The solution was filtered in the dark and the filtrate was evaporated by rotation evaporation to remove acetone and water until 25 mL of the filtrate was left. The filtrate was then freeze dried. The product, Pt(en)($NO_3$)$_2$ (m.w.=379.1), was checked by NMR, infrared absorption spectroscopy, and elemental analysis.

Preparation of Detectably Labeled (PtM) compounds

Examples 2–12 below describe the preparation of detectably labeled platinum compounds which are representative and illustrative of the invention. In each of Examples 2–12, Pt(en)($NO_3$)$_2$, prepared as described in Example 1 was labeled with a marker moiety. Typically, the described reactions were performed in the dark.

EXAMPLE 2
Preparation of Platinum Ethylenediamine BIOCYTIN-X Nitrate

BIOCYTIN-X (ε-((6-(biotinoyl)amino)hexanoyl)-L-lysine) is an example of a detectable hapten useful according to the invention. BIOCYTIN-X-labeled Pt(en) was prepared according to the following method. BIOCYTIN-X (31.6 mg, 0.065 mmol, Molecular Probes, Inc., of Eugene, Oreg., USA) was added to 15 mL filtered water in the dark and the mixture was heated slightly (up to a maximum of about 40° C.) until dissolving. The pH of the solution was adjusted pH 7–8 with 0.4M NaOH. Pt(en)($NO_3$)$_2$ (23.43 mg, m.w.= 379.1, 0.062 mmol) was added to 10 mL filtered water in the dark and the mixture was heated slightly (up to a maximum of about 50° C.), until the Pt(en)($NO_3$)$_2$ was completely dissolved. When both reagents were completely dissolved, the BIOCYTIN-X solution was added to the platinum solution and left to react for 210 minutes at room temperature in the dark. The pH of the solution monitored during the reaction and was maintained at about pH 7.0. The product [Pt(en)(BIOCYTIN-X)($NO_3$)$_2$]$NO_3$ was isolated by means of freeze drying.

Stability of the product was ensured by the binding of Pt not only to the amino group of BIOCYTIN-X but also to the carboxylate group of BIOCYTIN-X. Due to the latter binding kinetics of the platinum compound, a ring form is created which, it is believed, accounts for the stability of the product once it is dissolved in water, because no polymerization reactions can occur.

EXAMPLE 3
Preparation of Platinum Ethylenediamine BIOCYTIN Nitrate

In an alternative method, [Pt(en)(BIOCYTIN)($NO_3$)]$NO_3$ was prepared according to the following method. Pt(en)($NO_3$)$_2$ (0.0524 mmol, 36.2 mg) was added to 10 mL filtered water and heated to a maximum of about 50° C. until Pt(en)($NO_3$)$_2$ was completely dissolved. BIOCYTIN (ε-biotinoyl-L-lysine, 0.058 mmol, 37.5 mg, Molecular Probes, Inc.) was dissolved in 5 mL filtered water. The BIOCYTIN solution was added to the platinum solution and incubated while stirring 75 minutes at room temperature. The product was isolated by means of freeze drying. The product was checked by NMR and infrared absorption spectroscopy.

EXAMPLE 4
Preparation of Platinum Ethylenediamine-Digoxigenin-L-Lysine Nitrate

[Pt(en)(Digoxigenin)($NO_3$)]($NO_3$) was prepared according to the following method. Digoxigenin is a hydrolysis product of digoxin, and may be employed as a fluorescent label according to the invention. Pt(en)($NO_3$)$_2$ (0.062 mmol, 23.43 mg) was added to 10 mL demineralized water and heated to 50° C. until Pt(en)($NO_3$)$_2$ was completely dissolved. Digoxigenin-L-lysine (0.065 mmol, 31 mg, Boehringer Mannheim GmbH, Mannheim, Germany) was added to 10 mL demineralized water, and heated until all was dissolved. The two solutions were added together and reacted for 3 hours at room temperature. The end product was isolated by freeze drying.

EXAMPLE 5
Preparation of Platinum Ethylenediamine-Fluoresceinamine Nitrate

[Pt(en)(Fluoresceinamine)(NO$_3$)]NO$_3$ was prepared according to the following method. Pt(en)(NO$_3$)$_2$ (0.5 mmol, 189.55 mg) was dissolved in 20 mL methanol, by heating until dissolving. Fluoresceinamine (0.55 mmol, 191.01 mg, Sigma Chemical Co., St. Louis, Mis.) was dissolved in 20 mL methanol. The fluoresceinamine solution was then added to the platinum solution. An immediate change of color was observed. The reaction was run for 3 hours at room temperature. The crystalline end product was isolated by rotation evaporation.

EXAMPLE 6
Preparation of Platinum Ethylenediamine-5'-Acetamido-Fluorescein Nitrate

[Pt(en)(5'-acetamidofluorescein)(NO$_3$)]NO$_3$ was prepared according to the following method. Pt(en)(NO$_3$)$_2$ (0.047 mmol, 17.8 mg) was added to 5 mL methanol, and heated until it dissolved. 5'-iodoacetamidofluorescein (0.049 mmol, 20 mg, Molecular Probes, Inc.) was dissolved in 10 mL methanol. The iodoacetamidofluorescein solution was added to the platinum solution and reacted for 3 hours at room temperature. The end product was isolated by rotation evaporation.

EXAMPLE 7
Preparation of Platinum Ethylenediamine-ε-(6-(Fluorescein-5-Carboxamido)Rexanoyl)-L-Lysine Nitrate

[Pt(en)fluoresceinlysine(NO$_3$)]NO$_3$ was prepared according to the following method. Pt(en)(NO$_3$)$_2$ (0.077 mmol, 29.17 mg) was added to 10 mL methanol, and heated until dissolved. Epsilon-(6-(fluorescein-5-carboxamido) hexanoyl)-L-lysine (0.081 mmol, 50 mg, Molecular Probes, Inc.) was dissolved in 10 mL methanol. The fluorescein solution was added to the platinum solution and reacted for 3 hours at room temperature. The end product was isolated by rotation evaporation.

EXAMPLE 8
Preparation of Platinum Ethylenediamine-5-(and-6)-((N-(5-Aminopentyl)Amino)Carbonyl)Tetramethylrhodamine Nitrate

[Pt(en(tetramethylrhodamine cadaverine)(NO$_3$)]NO$_3$ was prepared according to the following method. Pt(en)(NO$_3$)$_2$ (0.074 mmol, 28 mg) was added to 10 mL methanol, and heated until dissolved. Tetramethylrhodamine cadaverine (0.077 mmol, 40 mg, Molecular Probes, Inc.) was dissolved in 10 mL methanol. The two solutions were mixed together and reacted for 3 hours at room temperature. The end product was isolated by rotation evaporation.

EXAMPLE 9
Preparation of Platinum Cascade Blue® Cadaverine Nitrate

Cascade Blue®, a tri-sulfonated pyrene available from Molecular Probes, Inc., is another fluorescent compound suitable for use as a detectable label according to the invention. Cascade Blue® is a registered trademark of Molecular Probes, Inc. [Pt(en)(Cascade Blue® cadaverine)(NO$_3$)]NO$_3$ was prepared according to the following method. Pt(en)(NO$_3$)$_2$ (0.057 mmol, 21.6 mg) was added to 10 mL demineralized water and heated to 50° C. until Pt(en)(NO$_3$)$_2$ was completely dissolved. Cascade Blue® cadaverine (0.06 mmol, 40 mg, Molecular Probes, Inc.) was dissolved in 10 mL demineralized water. The two solutions were mixed together and reacted for 3 hours at room temperature. The end product was isolated by freeze drying.

EXAMPLE 10
Preparation of Platinum(ethylenediamine) 4,4-Difluoro-5,7-Diphenyl-4-Bora-3a,4a-Diaza-S-Indacene-3-Propionyl-Ethylenediamine Nitrate The BODIPY® brand series of reagents from Molecular Probes, Inc., including 4,4-Difluoro-5,7-diphenyl-4-bora-3a,4a-diaza-s-indacene-3-propionyl-ethylenediamine, are fluorescent compounds which can be employed as a detectable label in the PtM compounds of the invention. BODIPY® is a registered trademark of Molecular Probes, Inc. [Pt(en)(BODIPY® 530/550 C3EDA)(NO$_3$)]NO$_3$ was prepared according to the following method. Pt(en)(NO$_3$)$_2$ (0.052 mmol, 19.66 mg) was added to 10 mL methanol, and heated until dissolved. BODIPY® 530/550 C3EDA (0.0545 mmol, 256 mg, Molecular Probes, Inc.) was dissolved in 10 mL methanol. The two solutions were mixed together and reacted for 3 hours. The end product was isolated by rotation evaporation.

EXAMPLE 11

Preparation of Platinum Ethylenediamine-Dansyl Lysine Nitrate

[Pt(en)(dansyl lysine)(NO$_3$)]NO$_3$ was prepared according to the following method. Pt(en)(NO$_3$)$_2$ (0.125 mmol, 47.5 mg) was dissolved in 20 mL demineralized water by heating to 50° C. until Pt(en)(NO$_3$)$_2$ was completely dissolved. Dansyl lysine (N-ε-(5-dimethylaminonaphthalene-1-sulfonyl)-L-lysine, 0.13 mmol, 50 mg, Molecular Probes, Inc.) was dissolved in 20 mL demineralized water, and the pH was adjusted to pH 7–8 with 0.4M NaOH. The two solutions were mixed together and reacted for 3 hours at room temperature. The end product was isolated by freeze drying.

EXAMPLE 12

Preparation of Platinum Ethylenediamine-5-Aminoeosin

Pt(en)(NO$_3$)$_2$ was linked to 5-aminoeosin according to the following protocol. Twenty-five (25) milligrams of 5-aminoeosin (0.0377 mmol, Molecular Probes, Inc.) was dissolved in 20 mL methanol under stirring at room temperature in the dark. Pt(en)(NO$_3$)$_2$ (13.8 mg, 0.0358 mmol) was dissolved in 10 mL methanol under stirring at slightly elevated temperature (<50° C.), in the dark. The Pt(en) solution was added to the eosin solution and stirred in the dark at ambient (room) temperature for 3 hours. The solvent was evaporated and the product recovered through rotation evaporation. The product was analyzed using NMR and elemental analysis.

EXAMPLE 13

Preparation of Platinum Ethylenediamine-IRD-40-Nitrate

[Pt(en)(IRD-40)(NO$_3$)]NO$_3$ was prepared according to the following method. IRD-40 (Li-Cor Inc., Lincoln, Neb.) has the following structure:

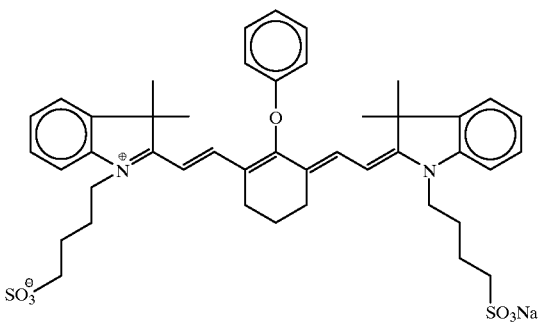

IRD-40 is first functionalized by reacting with an α,ω-diamine to introduce a strongly donating primary amine function yielding the following structure:

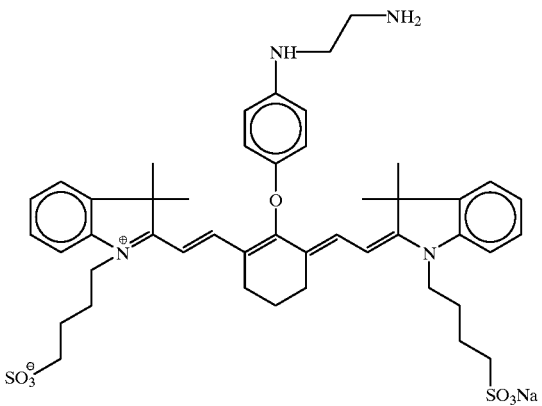

The terminal amine permits coupling to Pt(en)(NO$_3$)$_2$ without interfering with the basic skeleton of the dye.

Pt(en)(NO$_3$)$_2$ (0.008 mmol, 3.2 mg) was dissolved in 5 mL N,N-dimethylformamide with heating. Functionalized IRD-40 (0.009 mmol, 7.5 mg) was dissolved in 5 mL N,N-dimethylformamide. The IRD-40 solution was added to the platinum solution and reacted for 3 hours at room temperature. The end product was isolated by rotation evaporation.

EXAMPLE 14

Coupling of Pt(en) Compounds to DNA

This example describes a method of coupling a labeled Pt(en) compound of the invention to DNA. This reaction is typical of methods of labeling DNA molecules with PtM compounds of the invention. Other potential protocols would present themselves to the skilled artisan.

Five micrograms (μg) of double stranded DNA was sonicated (alternatively, DNase treated) to yield fragments of 300–500 bp. Six (6) μg of a detectably labeled Pt(en) compound was added and the volume was adjusted to 50 μl with demineralized water. The reaction mixture was incubated at 65° C. for 1 hour. Non-bound Pt(en) compound was blocked by adding 100 μL of a NaDDTC solution. The Pt(en) compound-labeled DNA was purified on a Sephadex G-50 column. Readily labeled and purified DNA was stored at −20° C. or used directly in a DNA probe based assay. It has been found that Pt(en) compound-labeled DNA probes can be stored at least 2 years at −20° C. without loss of activity and/or specificity.

EXAMPLE 15

Use of Pt-DNA Linkers in the Linked DNA Immunoassay Technique

Techniques are known in the art for quantitative analysis of nucleic acids. For example, the linked DNA immunoassay technique, described by Van Belkum et al., *J. Virol. Meth.*, 45:189–200 (1993), enables the quantitative analysis of small amounts of DNA (or RNA), e.g., after a polymerase chain reaction (PCR) amplification of the starting material. The technique is sensitive and specific, due to the use of specific DNA(RNA) probes and easy to perform, because of the quick DNA(RNA) Pt-labeling steps.

The linked DNA immunoassay technique is amenable to the use of the fast Pt-labeling compounds of the invention to label DNA or RNA probes. This technique is possible with inter alia the following three different approaches:

1. Linking DNA probe molecules to a surface of a substrate material by using a Pt compound. In this case a Pt compound of the invention is used as a bridge, binding DNA molecules irreversibly to a substrate surface such as plastic, nylon, or nitrocellulose. Detection of DNA targets can then be accomplished by using classically labeled DNA/RNA probes. Such methods are known in the art and include, for example, nick translation or chemical modification, random priming.

2. Linking a detectable group to the DNA, to render a DNA molecule into a DNA probe. Binding of DNA compounds to a surface can then be accomplished by using classical techniques, such as covalent linking to specially treated microtiter plates, baking of DNA molecules onto nitrocellulose, or binding of DNA molecules to nylon membranes.

3. A combination of techniques 1 and 2.

Approach 1

An immobilized DNA probe can be used to catch specific target molecules in a sample by using a hybridization technique. Detection of formed hybrids can be done by using different techniques, e.g., a second labeled DNA probe can be used to hybridize with a different site on the target DNA molecule to form a sandwich hybrid. The label can then be detected by using state of the art immunological detection and coloring techniques.

Approach 2

A volume containing (amplified) detectable DNA or RNA is directly labeled according to the protocol described in Example 14. Excess label is quenched by adding NaDDTC or thiourea. This approach distinguishes itself from other techniques by the fact that the target molecule is labeled in contrast to other assay in which labeled DNA or RNA probes are used to detect the target. The quick binding capacity of the Pt-label compound enables a DNA binding step as a routine step in a diagnostic test procedure (normal binding times are 60 minutes at 65° C.).

A second step is performed in a microtiter plate precoated with a target specific probe. Incubation is allowed to permit the formation of stable "labeled target" and probe hybrids. The direct labeling of target molecules enables the omission of laborious double hybridization techniques where one probe is used to catch the target and another labeled probe is used to detect the immobilized target.

In this method, the probes are covalently linked to the surface of the wells of the microtiter plate. The second incubation step has the character of a liquid hybridization and therefore can be performed very rapidly. This is one of the main innovative features of this approach to quantitative DNA hybridization techniques.

Approach 3

Both for the immobilization of DNA probes or DNA targets and for the labeling of DNA probes and targets, the newly developed Pt-labeling method of the invention can be used. These two DNA linking techniques can be combined into one assay, such as the polymerase chain reaction/oligonucleotide ligation assay (PCR/OLA), where both the "catcher" and the "detector" are linked to a second substance such as a detectable group, like biotin or digoxigenin, or a carrier surface, like a plastic stick, microtiter plate or a membrane.

Examples of the technique include the detection of sexually transmitted disease (STD)-related microorganisms in human diagnostics (e.g., Chlamydia, *syphilis,* HIV, Herpes, *gonorrhea,* hepatitis B,)

EXAMPLE 16
The Use of Pt-DNA Labels in Combination with Test Strip Procedures and Formats: The "DNA Dipstick"

The DNA dipstick technique enables the qualitative and semi-quantitative analysis of small amounts of DNA (or RNA), e.g., after a PCR amplification or freely present in samples of body fluids (blood, urine, sweat, etc.)

The technique is sensitive and specific, due to the use of specific DNA or RNA probes, and is easy to perform using compounds of the invention because of the quick DNA or RNA Pt-labeling steps.

The labeling characteristics of the newly developed Pt label can be used in a variety of ways to achieve a bound DNA or RNA molecule. For example, 1. It can be used to attach a detectable marker group to an oligo- or polynucleotide sequence;
2. It can be used to attach oligo- or polynucleotide sequences irreversibly to a solid phase (plastic, membranes, latex beads, hydrosols, or microtiter plate wells); or
3. A combination of 1 and 2 above.

The first type of labeling method involves a two-fold approach to the detection of biological analytes (hereinafter "biolytes") in test samples. A DNA probe can be labeled with the newly developed Pt labeling compound. This labeled probe can then be used to detect preformed hybrids on a membrane formed between the target DNA sequence and a primary probe. It is essential in this method that the primary probe recognizes a different sequence on the target than the secondary Pt-labeled probe. In practice, this can be achieved, for instance, with RNA hybridization where a poly-A probe is used as a primary probe to immobilize all RNA (recognizable by its poly-T tails) to a membrane.

The second approach differs slightly in that in this case the target can be labeled in the test sample fluid, because of the fast and very specific Pt labeling characteristics. A procedure like this would include a catch of the labeled target with an immobilized specific unlabeled DNA probe on a suitable membrane. Hence, a dipstick-based version of this method is contemplated for DNA/RNA applications.

To immobilize DNA probes or target DNA, a non-labeled Pt compound. i.e., a Pt compound with 2 free binding sites, can be used to act as a bridge between DNA and the surface of carriers (plastic, membrane, microtiter plates, etc.). Such Pt linker compounds are within the invention, as are substrate materials to which Pt compounds have been attached, leaving a site for attaching a probe biomolecule such as a nucleic acid. The compounds of the invention greatly enhance the usability of DNA sequences as catcher molecules in diagnostic assays, since there are few other substances known to science that readily bind DNA in a spontaneous way. With the introduction of this Pt bridge molecule, a wide field of new applications for the DNA technology has come within reach.

In the third preferred approach, a combination of the above-mentioned approaches is employed. Especially, the use of the Pt linker molecule in latex or hydrosol assays is particularly interesting. The linker enables the coupling of DNA molecules to small particles. The DNA molecules can then be hybridized to target material. A positive reaction is visualized by an agglutination of the particles, due to cross-linking among the hybrid DNA/particle compounds.

A test like this can readily be made quantitative. For example, the rate of agglutination can be tuned and measured at a specific wavelength. Especially, gold particles have the intrinsic characteristic that a shift in optimal wavelength occurs after agglutination.

EXAMPLE 17
Protein Labeling Using Pt-marker Compounds in Diagnostic Test Procedures The ability of Pt-marker compounds to interact with protein structures under specified conditions, that differ from the DNA binding conditions, can be used to detectably label various types of proteins. Examples of this approach include inter alia the labeling of:

a. monoclonal or polyclonal antibodies to detect primary targets in test samples;
b. protein derivatives used as antigens in test procedures based on the inhibition principle using an enzyme immunoassay capture test; and
c. specific protein structures that are known to interact specifically with other compounds, but generate a non-immunogenic interaction with each other, e.g., streptavidin and biotin, and protein A and G with immunoglobulins.

Labeled tracer molecules can be used to determine either qualitatively or quantitatively an amount of a certain biolyte in a suitable test format, e.g., dipsticks, ELISA, or others.

EXAMPLE 18
Long Term Acting Proteins

Of special interest is the in vivo use of the Pt linker to stabilize biomolecules, such as proteins. A therapeutical use of the Pt compounds of the invention is to overcome the problem of bioactive substances used as therapeutic agents or medicaments (insulin, factor VIII, and the like) having short term action once inside the body. The coupling of these substances to a Pt linker compound may enhance the half life of these molecules, thus enabling longer acting substances to be produced and used in vivo. This implies fewer complications for patients and more effective use of expensive drugs and medicines.

EXAMPLE 19
Detection of Platinated DNA Probes with the Silver-Enhancement Technique Platinated DNA or RNA probes of the invention are employed in hybridization methods to detect DNA or RNA sequences in sample material. The introduction of a platinum compound at the site of the target enables the deposition of silver in a chemical reaction especially designed to reduce ionic silver to metallic silver. At the site of a Pt nucleus, a decomposition of metallic silver (black) occurs due to the catalytic effect of the platinum nucleus.

Ionic silver ($Ag^+$) is reduced by a reducing agent (e.g., Na-borohydride, hydroquinone) in solution. In a constant ratio, the amount of silver deposited on the platinum is proportional to the length of the enhancement incubation. Visualization of a non-visible platinum nucleus can be accomplished by the empirical observation of the appearance of a black spot in the test sample. A black spot indicates the site of specific probe binding and thus the site of specific target location. The technique enables a quick and easy diagnostic procedure for the detection of various microorganisms and gene translocations/abnormalities.

EXAMPLE 20
Coupling of Pt(en) Compounds to Proteins

This example describes a method of coupling a labeled Pt(en) compound of the invention to a mouse monoclonal antibody. This reaction is typical of methods of labeling proteins with PtM compounds of the invention.

A solution of a mouse monoclonal antibody MH16-1 (anti-human IgG, Mw 150,000, Central Laboratory of Blood Transfusion, Amsterdam, The Netherlands) was prepared in 20 mm Tris buffer to a concentration of 1 mg/mL. The pH of the solution was adjusted to a final pH of between 9 and 10, by adding 1M carbonate buffer pH 10.

A solution of 1 $\mu$g/mL [Pt(en)(fluoresceinamine)(NO$_3$)]NO$_3$ (PtF, Example 5) was prepared in methanol. Equal volumes of the PtF solution and 40 mM Tris buffer pH 9.5 were mixed. One thousand (1,000) $\mu$L of the MH16-1 solution were mixed with 1,000 $\mu$L of the PtF solution, giving a final molar ratio of protein:PtF=1:100. The mixture was incubated with continuous stirring for 4 hours at room temperature, and then for 16 hours at 4° C. The unbound PtF compound was removed by size exclusion chromatography over a Sephadex® G25 fine column.

In a spectrophotometer, the extinction of the labeled protein was measured at 280 and 495 nm. The E280/E495 ratio was used to determine the molar ratio of binding of PtF to protein, by means of the relationship PtF/protein (molar)= 3/(E280/E495–0.35). This molar ratio was about 3, indicating optimal labeling.

The biological activity of the labeled monoclonal antibody was measured in a routine enzyme immunoassay with human IgG as the antigen coating of the wells and an anti-fluorescein antibody conjugated to horseradish peroxidase. In parallel negative control experiments, the protein binding of fluorescein itself was compared to that of PtF, and the molar ratio of fluorescein binding was less than 0.002.

EXAMPLE 21
Preparation of PtF for Labeling Purposes

Fluorescein-NH(CS)NHCH$_3$ was prepared by reacting 100 mg fluorescein-N=C=S (fluorescein-5-isothiocyanate, abbreviated FITC, 0.257 mmol, Molecular Probes, Inc.) with 1 mL CH$_3$NH$_2$ in 100 mL water. The reaction required about 1 hour under continuous stirring at room temperature in the dark. The obtained reaction product, fluorescein-NH(CS)NHCH$_3$, was precipitated from the solution by acidifying with 1M HCl to pH 2–3. The precipitate was washed in water and then collected.

Then a suspension of 100 mg (0.237 mmol) of the thus obtained fluorescein-NH(CS)NHCH$_3$ in 95 mL of water was brought with NaOH (1M) to pH 10–11, whereby a bright yellow solution was obtained. To this solution was added 72 mg (0.178 mmol) of [Pt(ethylenediamine)(Me$_2$SO)]Cl in 5 mL of water and the reaction mixture was slowly stirred in the dark for 5–10 minutes at room temperature. The non-reacted fluorescein-NH-(CS)NHCH$_3$ was precipitated by acidification to pH 2–3 with HCl (1M) and removed by filtration. The bright yellow filtrate was freeze-dried, yielding a stable dry compound {Pt(ethylenediamine)(Me$_2$SO)(fluorescein-NH(CS) NHCH$_3$)}. Alternatively, [Pt(ethylenediamine)Cl$_2$]Cl may be employed to yield {Pt(ethylenediamine)Cl(fluorescein-NH(CS)NHCH$_3$)}. Either of these compounds may also be referred to herein as "PtF").

In principle, the reaction described above may be carried out in an analogous manner for marker moieties other than fluorescein, for instance, rhodamine, aminomethylcoumarine (AMCA), biotin, digoxigenin, or any other detectable label or hapten, which may be modified in such a manner that therein is present a double-bonded sulfur (=S) atom, a —SR group, a —NR'R" group or a nitrogen ring (—N—), wherein R, R', and R" are the same or different and represent hydrogen or an organic residual group. These S- or N-containing groups serve as a binding ligand through which the platinum (Pt) atom can bind to the marker moiety.

EXAMPLE 22
Nucleic Acid Labeling with PtF

This example illustrates a preferred method for labeling of nucleic acid with a typical platinum-based marker compound of the invention. The dry PtF compound of Example 19 is dissolved at a concentration of 1 mg/mL in distilled water, which is brought to pH 9–10 with NaOH. Then DNA (single or double stranded) or RNA at any suitable concentration (e.g., 100 $\mu$g/mL) is taken up in a low-salt buffer with a pH of about 8 (for instance, 10 mM Tris-HCl) and possibly fragmented by ultrasonication. To the thus obtained nucleic acid solution a ten-fold molar excess of the PtF solution is added and after proper mixing the reaction mixture is incubated in the dark at room temperature for 30–60 minutes. Next, 1/10 volume part of a sodium acetate (3M) solution of pH 5.6 is added to the reaction mixture and, after mixing, subsequently two parts of ethanol are added, after which it is thoroughly stirred. The reaction vial is then incubated for 15 minutes at 80° C. or for 2 hours at –20° C. The PtF-labeled nucleic acid is thereupon precipitated by centrifugation at 10,000×g for 7 minutes. The obtained pellet is washed in 90% ethanol and the nucleic acid labeled with the PtF is dissolved at the desired concentration in a buffer (e.g., 10 mM TRIS-HCl, pH 7.5, 0.3 mM EDTA). The Pt labeled nucleic acid is now ready for use.

Examples of the Use of PtM-Labeled Nucleic Acids

EXAMPLE 23
Viral Diagnostics

Human papilloma virus cannot be cultured, but some subtypes (HPV 16/18) are positively connected with the origin of malignant tumors of amongst others the cervix and the penis. By now labeling purified DNA of such a papilloma virus with PtM and then performing an in situ hybridization procedure on cells or tissue of for instance the cervix, the presence of the risk-bearing type of papilloma virus may be shown very specifically by means of a direct fluorescence procedure or an indirect immunohistochemical procedure with anti-PtM antibodies.

EXAMPLE 24
Viral Diagnostics a) Pt-labeled probes according to the invention are developed for inter alia the detection of DNA (Vaccinia, herpes simplex (HSV1/1, Epstein Barr, and adenovirus)) and RNA viruses (Rota virus, influenza A, Coxsackie B). Previously, the diagnosis of acute infection with Hepatitis B virus has only been possible by inoculation of chimpanzees, for the virus cannot be cultured in human cells.

b) Varicella zoster virus (VZV), too, is very difficult to culture: typically culture times of 5–14 days are required before a culture may be assessed. Moreover, the virus is very labile and may become inactivated during transport. A negative test is therefore no proof of absence of the illness. In addition, VZV infection is on morphological grounds indistinguishable from infections with herpes simplex virus. Even commercially available antisera do not give a definitive answer in immunohistochemical tests.

c) cytomegalovirus is very laboriously cultured; diagnoses within a week's time are impossible, with 6 weeks of culture time being unexceptional. CMV infections form an important source of complications in transplant patients and in patients with reduced immune defenses (e.g., in AIDS). Good monitoring of these patients is essential.

In the above-mentioned cases a, b and c, which figure as only some of the many possibilities of examples of viral diagnostics, diagnostics are considerably simplified and accelerated by the application of hybridization techniques with PtM-labeled probes of the invention.

EXAMPLE 25

Bacterial Diagnostics

Recently, it has become possible to detect bacterial nucleic acids using DNA probes. The presence of genes for bacterial toxins can also be detected. However, it has not previously been possible to discern whether these genes are expressed. Fast detection of chromosomal and plasmid coded virulence factors (amongst others *Listeria monocytogenes, Clostridium perfringens* enterotoxin, *Vibrio cholerae* enterotoxin, *E. coli* enterotoxins and invasivity, *Shigella* and *Yersinia enterocolitica* enteroinvasivity) are important applications of the compounds and methods of the present invention in the diagnosis of food poisoning as well as in quality control in the food industry (end product control). Detection of *Helicobacter* (formerly Campylobacter) *pylori* by DNA in situ hybridization with PtM probes in stomach biopsies of patients with gastritis is also now possible. Also, the DNA of *Chlamydia trachomatis* may be detected by the PtM compounds in, for instance, a sandwich assay, or by means of an in situ hybridization using the inventive compounds and methods.

EXAMPLE 26

Diagnostics of Parasitic Infections

World-wide 2 million people each year pass away due to malaria. In principle, this can be prevented by timely correct diagnostics. The present microscopic methods are often all too complicated for routine practice in third world countries. In the western world the difficult microscopic technique may now be extended with in situ hybridization on routine preparations, using the PtM probes of the invention. Through this means, the differential diagnosis of malaria species is considerably simplified and can be carried out by minimally trained personnel. In the third world, a dipstick test based on the present PtM compounds is an appropriate route for fast and simple diagnostics. Analogous examples include valid infection illnesses caused by Schistosoma, Trypanosoma, toxoplasmas, etc.

EXAMPLE 27

Detection of Genetic Deviations

The hybridization technique with PtM probes offers the possibility for prenatal diagnostics of congenital deviations in for instance amniotic fluid punctates and chorionbioses. Postnatal detection of deviations (for instance malignities) is also possible, as well as extension of HLA typification for diagnosis of HLA-associated illnesses.

Restriction fragment length polymorphisms (RFLPs) may also be detected with the PtM compounds of the invention. Every human genome will be digested, when treated with restriction enzymes, to produce a large number of specific fragments known as restriction fragments. If by a mutation the base sequence changes at a site at which a restriction enzyme attacks, this will lead to the development of aberrant fragments. These fragments may be detected by suitable (PtM-labeled) probes by means of DNA blotting methods. This approach is suitable in many situations, including in genetic diseases such as sickle cell anemia, Duchenne muscular dystrophy, cystic fibrosis, Huntington's chorea).

Immediate detection of aberrant DNA with synthetic oligonucleotide probes may take place when the base sequence belonging to a DNA deviation is known (e.g., β-thalassemia, antithrombin III deficiency, growth hormone deficiency, hemophilia B, PKU, etc.).

Detection of chromosome changes, such as translocations, deletions, inversions, and duplications, in the human karyotype may be detected by means of in situ hybridization followed by direct PtF fluorescence, or by Southern blotting of restriction fragments.

EXAMPLE 28

Detection of Gene Expression

The visualization of the presence of a cellular antigen using immunochemical techniques does not prove that at that moment the gene encoding the antigen is expressed. Neither does this indicate whether the detected product has an intra- or extracellular origin. Detection of mRNA within a cell may now be accomplished using the PtM compounds of the invention to give direct information about the expression of genes. This information may provide data on cell functioning, but may also be of assistance in diagnostics.

It is known that the RNA in situ hybridization (RISH) technique can be limited in sensitivity by the size of the labeling moiety. Commonly, 90% or more of the mRNA in cells and tissues is inaccessible to larger nucleic acids and proteins in solution. Typically, only the very small portion of the mRNA which occurs at the surface of cells or tissue sections can be reached. Constraints on the size of the marker moiety have generally entailed the use of radiolabels rather than fluorescent molecules or other larger groups such as enzymes or avidins. Previously, other problems with this technique have arisen, in particular, due to the necessity of disposing of an immunohistochemical detection system including radiolabels. These problems may, however, be avoided with the application of direct PtM fluorescence. In view of present problems in carrying out the RNA in situ hybridization technique with non-radioactive probes, the application of the very direct PtM label is an advantageous way of performing such diagnostics.

Detection of deviating mRNA as a mark of heritable illnesses by means of blotting with radioactive cDNA probes has been proven to be possible already for a number of congenital deviations. The speed and applicability of this type of technique may be considerably increased by means of non-radioactive (or radioactive) PtM labeling.

With PtM probes, RISH or blotting may be applied in the diagnosis of cancer by means of detection of specific gene transcripts (for instance, calcitonin mRNA in thyroid gland metastases, oncogene expression in malignant tumors), or the loss of germ line bands (loss of heterozygosity) or gene rearrangement (lymphomas).

Thus, while there have been described what are presently believed to be the preferred embodiments of the present invention, those skilled in the art will realize that other and further embodiments can be made without departing from the spirit of the invention, an it is intended to include all such further modifications and changes as come within the true scope of the claims as set forth herein.

What is claimed is:

1. A detectable label compound, having the structure:

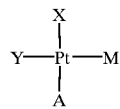

wherein:
Pt is a platinum atom;
N is a detectable marker moiety;
A is a displaceable leaving group; and
X and Y are stabilizing substituents.

2. A kit for labeling a biomolecule, comprising a container housing a detectable label compound as defined in claim 1.

3. The detectable label compound of claim 1, where M comprises a detectable marker moiety selected from the group consisting of radioactive labels, enzymes, specific binding pair components, colloidal dye substances, fluorochromes, chromogens, reducing substances, colored latex sols, metal sols, particulate sols, dansyl lysine, antibodies, protein A, and protein G.

4. The detectable label compound of claim 3, wherein M comprises a fluorescent group selected from the group consisting of fluoresceins, eosins, trisulfonylpyrenes, rhodamines, digoxigenins, and 4,4-difluoro-4-bora-3a,4a-diaza-s-indacenes.

5. The detectable label compound of claim 3, wherein M comprises a specific binding pair component selected from the group consisting of biotins, iminobiotins, avidins, streptavidins, and biocytins.

6. The detectable label compound of claim 1, wherein X and Y are interconnected forming a stabilizing bridge moiety.

7. The detectable label compound of claim 6, wherein the stabilizing bridge moiety comprises an aliphatic diamine having 2–6 carbon atoms.

8. The detectable label compound of claim 7, wherein the stabilizing bridge moiety comprises ethylenediamine.

9. The detectable label compound of claim 1, wherein A is a displaceable leaving group selected from the group consisting of ligands which are displaced substantially irreversibly by a biomolecule.

10. The detectable label compound of claim 9, wherein A is a displaceable leaving group selected from the group consisting of halogens, $SO_3^{2-}$, $NO_3^-$, $PO_4^{3-}$, $CO_3^{2-}$, analogs thereof including ethylnitrate; phosphonates, carboxylates, oxalates, citrates, and derivatives thereof; $H_2O$; ROH and $RO^-$, in which R is an organic residual group; and substituted sulfoxides $R^1R^2SO$, in which $R^1$ and $R^2$, whether or not identical to each other, represent organic residual groups.

11. The detectable label compound of claim 9, wherein A is a displaceable leaving group selected from the group consisting of $(CH_3)_2SO$, Cl, and $H_2O$.

12. A platinum-based binding substance, having the structure:

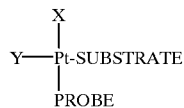

wherein:
Pt is a platinum atom;
PROBE is a probe biomolecule for associating to a target biomolecule;
SUBSTRATE is a substantially solid material; and
X and Y are stabilizing substituents.

13. The platinum-binding substance of claim 12, wherein said substrate is selected from the group consisting of gels, resins, beads, nitrocellulose, nylon filters, microtiter plates, and culture flasks.

14. A method for selectively binding a target biomolecule comprising:
contacting a sample, comprising said target biomolecule, with a platinum-based binding substance as defined in claim 12.

15. A diagnostic kit for binding a target biomolecule, comprising:
a platinum-based binding substance as defined in claim 12, and
a container.

* * * * *

UNITED STATES PATENT AND TRADEMARK OFFICE
CERTIFICATE OF CORRECTION

PATENT NO. : 5,985,566
DATED : November 16, 1999
INVENTOR(S) : Houthoff, et al.

It is certified that error appears in the above-identified patent and that said Letters Patent is hereby corrected as shown below:

<u>In Column 7, line 24</u>, now reads "The diagnostic is kit"; should read --The diagnostic kit--.

<u>In Column 19, line 29</u>, now reads "(Fluorescein-5-Carboxamido)Rexanoyl)-"; should read --(Fluorescein-5-Carboxamido)Hexanoyl)--.

<u>In Column 29, line 12</u>, now reads "N is a detectable marker moiety;"; should read --M is a detectable marker moiety;--.

Signed and Sealed this

Fourteenth Day of November, 2000

Attest:

Q. TODD DICKINSON

Attesting Officer     *Director of Patents and Trademarks*